United States Patent [19]

Matsumura

[11] Patent Number: 4,962,764
[45] Date of Patent: Oct. 16, 1990

[54] HEMOSTATIC UNIT FOR MEASURING ARTERIVENOUS BLOODSTREAMS

[75] Inventor: Mitsuma Matsumura, Tokyo, Japan
[73] Assignee: Nikki Co., Ltd, Japan
[21] Appl. No.: 377,331
[22] Filed: Jul. 10, 1989
[30] Foreign Application Priority Data
    Sep. 2, 1988 [JP] Japan .................. 63-115015[U]
[51] Int. Cl.⁵ .......................................... A61B 5/0295
[52] U.S. Cl. ..................................... 128/691; 128/685; 128/694
[58] Field of Search ................. 128/672, 677–686, 128/691, 694; 600/201–203

[56] References Cited

U.S. PATENT DOCUMENTS

| | | | |
|---|---|---|---|
| 4,566,463 | 1/1986 | Taniguchi et al. | 128/682 |
| 4,567,899 | 2/1986 | Kamens et al. | 128/680 |
| 4,660,567 | 4/1987 | Kaneko et al. | 128/680 X |
| 4,768,518 | 9/1988 | Peltonen | 128/677 |

Primary Examiner—Angela D. Sykes
Attorney, Agent, or Firm—King & Schickli

[57] ABSTRACT

A hemostatic unit for the determination of arteriovenous bloodstreams comprises a flat cuff (15) having a length sufficient to be wound by about one and a half turns around the region to be measured and being chargeable with compressed air, a pump (11, 21) for feeding said compressed air into said cuff (15), a pressure regulating valve (13, 23) for regulating the pressure of said compressed air, an air supply/discharge circuit for connecting an outlet (11a, 21a) of said pump (11, 21) to an air inlet (15b) of said cuff (15), and an air suction circuit branching out of said air supply/discharge circuit and connected to an inlet of said pump (11, 21). The unit further includes an electromagnetic valve (12, 22, 22') provided in said air/supply circuit and said air suction circuit with its given valve port being in open communication with the atmosphere.

1 Claim, 3 Drawing Sheets

HEMOSTATIC UNIT FOR MEASURING ARTERIVENOUS BLOODSTREAMS

BACKGROUND OF THE INVENTION

1. Field of the Invention

The present invention relates to a hemostatic unit for measuring arteriovenous bloodstreams, which is adapted to apply hemostatic treatment to the region to be measured, when arteriovenous bloodstreams are determined for clinical diagnoses, etc. by plethysmography.

2. Prior Art

Referring to the measurement of arteriovenous bloodstreams by plethysmography, a measuring strain gauge 42 is wound around the lower limb with a cuff 43 being wound around the thigh, as illustrated in FIG. 4 by way of example. An amount of compressed air is supplied to the cuff 43 to expand it for hemostatic purposes, and that state is kept for a certain period of time. Then, the internal pressure of the cuff 43 is reduced by spontaneous evacuation to electrically determine the arteriovenous bloodstreams by means of the strain gauge 42.

With such a conventional unit, however, it is impossible to obtain any rapid pressure drop required for plethysmometry and, hence, difficult to achieve any accurate determination, since the internal pressure of the cuff is reduced by spontaneous evacuation. Even when an assistant then attempts to remove the cuff to achieve complete pressure reductions, it is impossible to obtain any uniform pressure reductions. Besides, such an attempt is timeconsuming and fails to give any value of high accuracy.

SUMMARY OF THE INVENTION

In view of the foregoing, an object of the present invention is to provide rapid and precise determination of arteriovenous bloodstreams by pressurizing a cuff to a precise and given pressure and providing rapid and uniform reduction of the internal pressure of the cuff by forced evacuation.

According to the present invention, the above object is achieved by the provision of a hemostatic unit for the determination of arteriovenous bloodstreams comprising in combination:

a flat cuff having a length sufficient to be wound by about one and a half turns around the region to be measured and being chargeable with compressed air, a pump for feeding said compressed air into said cuff, a pressure regulating valve for regulating the pressure of said compressed air, an air supply/discharge circuit for connecting an outlet of said pump to an air inlet of said cuff, and an air suction circuit branching out of said air supply/discharge circuit and connected to an inlet of said pump, and further including an electromagnetic valve provided in said air/supply circuit and said air suction circuit with its given valve port being in open communication with the atmosphere.

While the cuff is wound around the region to be measured, the pump is actuated with a switch for the electromagnetic valve being put on. Thereupon, the compressed air is supplied to the cuff through the air supply/discharge circuit which connects the outlet of the pump to the air inlet of the cuff, and is then regulated to a given pressure by the pressure regulating valve to pressurize and expand the cuff, while allowing the air suction circuit to be in open communication with the atmosphere. After the region to be measured is kept hemostatic for a certain period of time by the pressurization of the cuff, the electromagnetic valve is switched over to a reversal mode in which the air supply/discharge circuit is allowed to be in open communication with the atomsphere simultaneously with the connection of the air suction circuit to the cuff, whereby the compressed air remaining within the cuff is forcedly sucked under the sucking action of the pump and evacuated to the atomsphere. Under the action of such forced evacuation, the internal pressure of the cuff is rapidly reduced to restore it to the unexpanded state.

BRIEF DESCRIPTION OF THE DRAWINGS

The present invention will now be explained with reference to the accompanying drawings, which are given for the purpose of illustration alone and in which.

DESCRIPTION OF THE PREFERRED EMBODIMENT

Figure 3A:
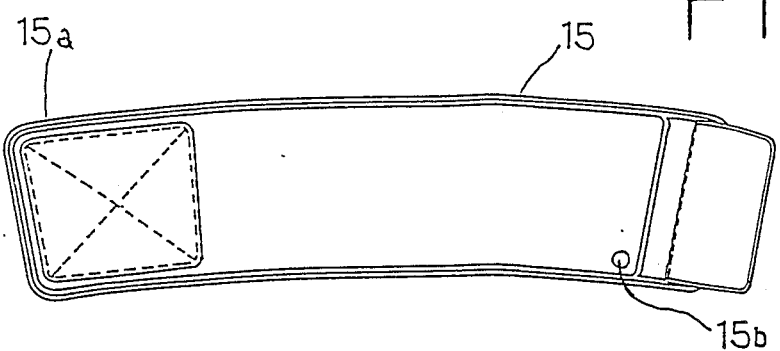
FIG. 3 shows the cuff according to the present invention with A and B being plan and bottom views, respectively.
Figure 3B:
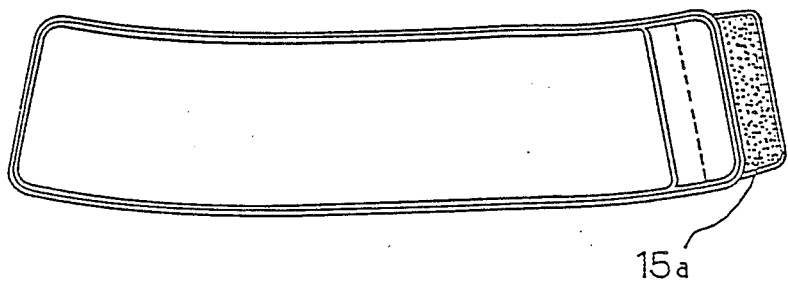
Figure 4:
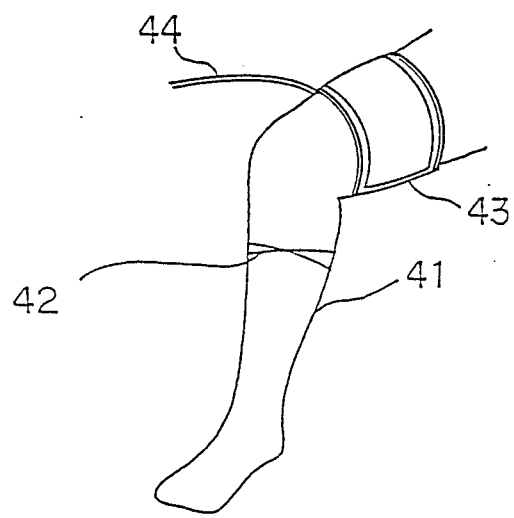
FIG. 4 is a view illustrative of the determination of bloodstreams by plethysmography.

Referring first to FIGS. 3(A) and 3(B), a cuff shown generally at 15 is formed of an expandable bag member which is of a rectangular and flat shape, as illustrated. The configuration and size of the cuff 15 may vary depending upon the region to be determined in terms of bloodstream. The cuff 15 is provided at one end of its back side with a hook for a belt fastener 15a and on a suitable portion of its front side with a hook for said belt fastener 15a. It is understood that the belt fastener 15a is required to maintain its clamp force during use, since the cuff 15 is designed to be charged with compressed air of a pressure sufficient to keep hemostatic the region to be measured (for instance, a pressure of 50 mm Hg required for arterial hemostasis to 250 mm Hg needed for venous hemostasis). In order to obtain sufficient clamp force to this end, it is preferred for the cuff 15 to have an increased area of contact with the region to be measured or be of a length sufficient to be wound by about one and a half turns around the region to be measured.

Figure 1A:
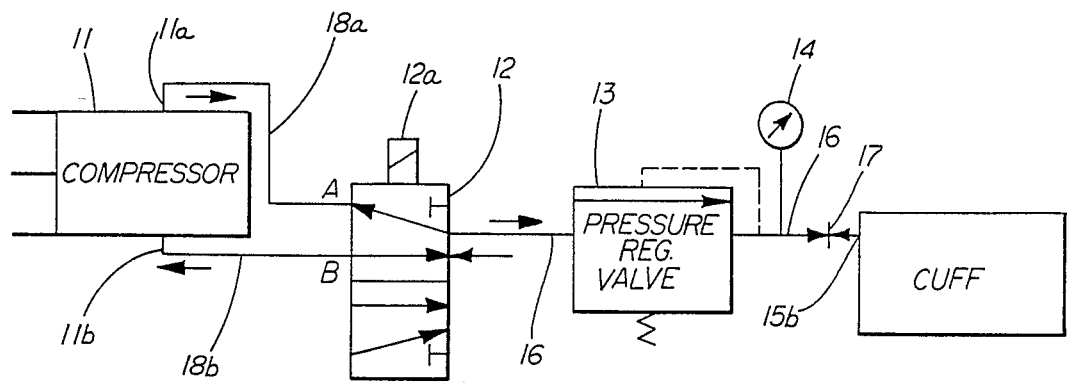
FIG. 1 is a circuit diagram of one embodiment of the present invention with A and B showing the cuff during pressurization and depressurization, respectively.
Figure 1B:
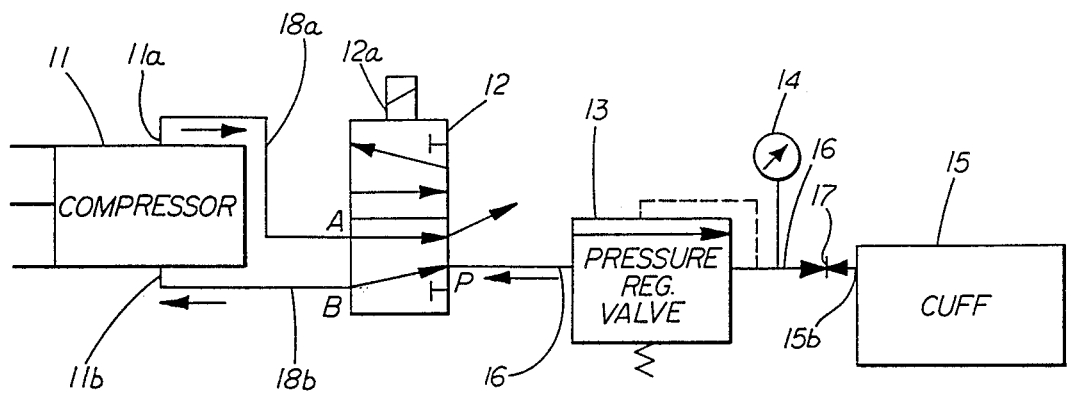

As illustrated in FIGS. 1(A) and 1(B), the cuff 15 is detachably connected to a cuff's side conduit 16 through a joint 17 connected to an air inlet 15b in said cuff 15. A compressor, which is generally shown at 11 and used as a pump, has its outlet port 11a connected through a conduit 18a to an A port of a single electromagnetic changeover valve, i.e., a five-port/two-position electromagnetic valve 12 and its inlet port 11b connected through a conduit 18 b to a B port of said electromagnetic valve 12. On the other hand, a P port of the electromagnetic valve 12 is connected with the cuff's side conduit 16, and between the cuff's side conduit 16 and the cuff 15 there is interposed a pressure regulating valve 13 adapted to freely regulate the pressure of compressed air supplied to the cuff 15.

As will be appreciated from the foregoing, an air supply/discharge circuit is defined by the conduit 18a and the cuff's side conduit 16, whereas an air suction circuit is defined by the conduit 18b. It is noted that a pressure gauge 14 provides a visual indication of the pressure in the conduit 16.

Referring to FIG. 1(A), a first operative position is shown wherein an amount of compressed air is supplied to the cuff 15 to pressurize it. For that purpose, a solenoid 12a of the five-port/two-position electromagnetic valve 12 is energized to allow the port B, i.e., the conduit 18b to be in open communication with the atmosphere, thereby feeding air to the compressor 11. On the other hand, the conduit 18a is connected to the cuff's side conduit 16 through the ports A and P to supply the compressed air from the compressor 11, regulated to a given pressure through the pressure regulating valve 13, into the cuff 15, thereby pressurizing the interior thereof.

Referring to FIG. 1(B), a second operative position is shown wherein the compressed air is forcedly evacuated from within the cuff 15. For that purpose, the solenoid 12 a is deenergized to connect the cuff's side conduit 16 to the conduit 18b through the ports P and B, whereby the compressed air is on the one hand sucked from within the cuff 15 and the port A, i.e., the conduit 18b is on the other hand allowed to be in open communication with the atmosphere. Thus, the compressed air is sucked from within the cuff 15 to the compressor 11 and forcedly discharged to the atmosphere through the conduit 18a, so that the internal pressure of the cuff 15 is rapidly reduced.

It is noted that the energization or deenergization of the above solenoid 12a is attained by a switch, not shown.

Figure 2A:
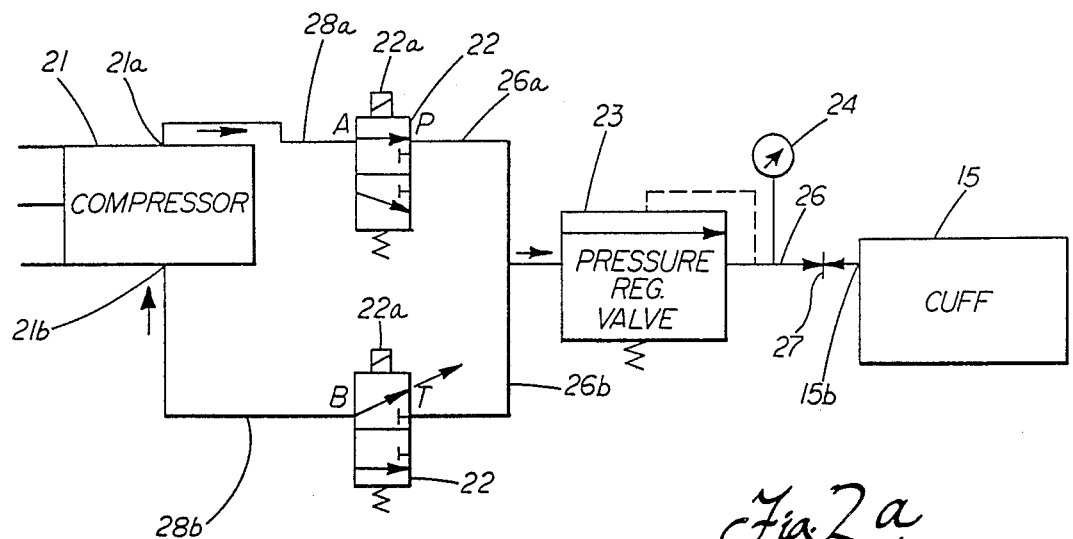
FIG. 2 is a circuit diagram of another embodiment of the present invention with A and B showing the cuff during pressurization and depressurization, respectively.
Figure 2B:
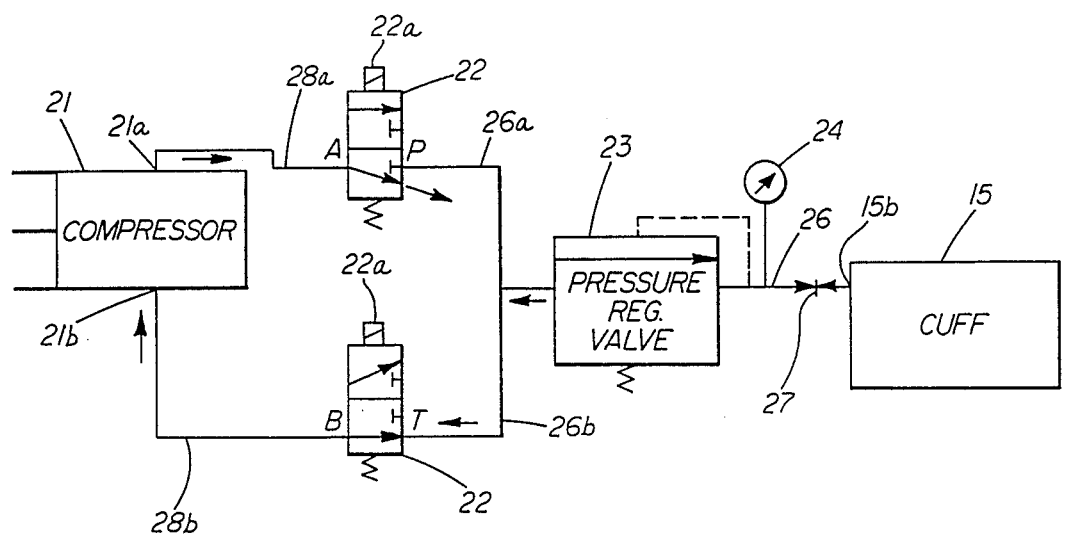

In a second embodiment illustrated in FIGS. 2(A) and 2(B), two electromagnetic valves, i.e., first and second three-port/two-position electromagnetic changeover valves 22 and 22' are used in place of the above five-port/two-position electromagnetic valve 12. In this embodiment, the outlet 21a and inlet 21b of a compressor 21 are connected through conduits 28a and 28b to ports A and B of the first and second electromagnetic valves 22 and 22', respectively. A port P of the first electromagnetic valve 22 is connected with a conduit 26 a and a pressure regulating valve 23, whereas a port T of the second electromagnetic valve 22' is similarly connected with a conduit 26b and the pressure regulating valve 23. It is appreciated that a structure from the pressure regulating valve 23 to a cuff 15 is similar to that of the first embodiment illustrated in FIGS. 1(A) and 1(B).

As will be understood from the foregoing, an air supply/discharge circuit is defined by the conduits 28a, 26a and 26, whereas an air suction circuit is defined by the conduits 28b and 26b.

Referring to FIG. 2(A), a first operative position is shown wherein an amount of compressed air is supplied into the cuff 15 to pressurize it. For that purpose, the solenoids 22a and 22'a of the first and second electromagnetic valves 22 and 22' are synchronously energized to permit the port B of the second electromagnetic valve 22', i.e., the conduit 28b to be in open communication with the atmosphere, thereby feeding air into the compressor 21. On the other hand, the conduit 28a is connected to the conduit 26a through the ports A and P to supply the compressed air from the compressor 21, regulated to a given pressure through the pressure regulating valve 23, into the cuff 15, thereby pressurizing the interior thereof.

Referring to FIG. 2(B), a second operative position is shown wherein the compressed air is forcedly evacuated from within the cuff 15. For that purpose, the solenoids 22 a and 22'a are synchronously deenergized to connect the conduit 26b to the conduit 28b through the ports B and T, whereby the compressed air is on the one hand sucked from within the cuff 15, and the port A, i.e., the conduit 28a is on the other hand allowed to be in open communication with the atmosphere. Thus, the compressed air is sucked from within the cuff 15 to the compressor 21 and forcedly discharged to the atmosphere through the conduit 28a, so that the internal pressure of the cuff 15 is rapidly reduced.

Although one-side solenoids are used in this embodiment, it is understood that both-side solenoids may be similarly used.

The present invention constructed as mentioned above has the following effects.

Since the pressure of the compressed air supplied to the cuff is regulatable by the operation of the pressure regulating valve, it is possible to regulate the cuff's internal pressure to the proper pressure needed for the determination of bloodstreams depending upon the subject or region to be determined. Furthermore, since the pump can be easily switched over from its discharge mode to its intake mode by the operation of the electromagnetic valve(s) and vice versa, it is possible to achieve rapid evacuation of the compressed air from within the cuff, resulting in rapid and accurate determination of arteriovenous bloodstreams by plethysmography.

While the present invention has been described with reference to the specific embodiments illustrated in the drawings, it is understood that many other modifications or changes may be possible without departing from the scope and spirit of the present invention as defined in the appended claim.

What is claimed is:

1. A hemostatic unit for the determination of arteriovenous bloodstreams comprising in combination:
   a flat cuff (15) having a length sufficient to be wound by at least about one and a half turns around the region to be measured and being chargeable with compressed air;
   pump means (11, 21) including an outlet port (11a, 21a) for supplying said compressed air into said cuff (15) and an inlet port (11b, 21b) for discharging said compressed air charged into said cuff (15);
   pressure regulating valve means (13, 23) for regulating the pressure of said compressed air supplied to said cuff (15);
   air supply/discharge circuit means interposed between said pump means (11, 21) and said cuff (15) and including said pressure regulating valve means (13, 33), and
   changeover valve means (12, 22, 22') interposed between said pump means (11, 21) and said pressure regulating valve means (13, 23), said changeover valve means being selectively operable in a first position to connect said outlet port (11a, 21a) of said pump means (11, 21) with said cuff (15) and said inlet port (11b, 21a) of said pump means (11, 21) with atmosphere and in a second position to connect said outlet port (11a, 21a) of said pump means (11, 21) with atmosphere and said inlet port (11b, 21b) of said pump means (11, 21) with said cuff (15) so as to positively draw air from said cuff (15).

* * * * *